United States Patent [19]

Wahlig et al.

[11] 4,347,234

[45] Aug. 31, 1982

[54] MEDICINALLY USEFUL, SHAPED MASS OF COLLAGEN RESORBABLE IN THE BODY

[75] Inventors: Helmut Wahlig, Darmstadt; Elvira Dingeldain, Dreieich; Dietrich Braun, Darmstadt-Arheilgen, all of Fed. Rep. of Germany

[73] Assignee: Merck Patent Gesellschaft mit beschrankter Haftung, Darmstadt, Fed. Rep. of Germany

[21] Appl. No.: 273,291

[22] Filed: Jun. 15, 1981

Related U.S. Application Data

[62] Division of Ser. No. 82,520, Oct. 9, 1979, Pat. No. 4,291,013.

[30] Foreign Application Priority Data

Jan. 9, 1978 [DE] Fed. Rep. of Germany ....... 2843963

[51] Int. Cl.³ .......... A61K 9/22; A61K 9/26; A61F 13/00; A61L 15/03
[52] U.S. Cl. .................... 424/15; 424/16; 424/19; 424/21; 424/22; 424/28; 424/36; 424/177; 424/359; 424/14; 128/260; 128/335.5; 3/1.9; 3/1.91
[58] Field of Search ............... 424/14, 15, 16, 19, 424/21, 22, 28, 36, 177, 359; 128/260, 335.5; 3/1.9, 1.91

[56] References Cited

U.S. PATENT DOCUMENTS

| | | |
|---|---|---|
| 2,967,802 | 1/1961 | Towby et al. ............... 424/92 |
| 3,126,884 | 3/1964 | Tucker . |
| 3,322,632 | 5/1967 | Schwick et al. ............ 424/88 |
| 3,400,199 | 9/1968 | Balana . |
| 3,435,110 | 3/1969 | Nichols ...................... 424/20 |
| 3,435,117 | 3/1969 | Nichols ...................... 424/359 |
| 3,443,261 | 5/1969 | Battista et al. |
| 3,458,397 | 7/1969 | Myers et al. |
| 3,469,003 | 9/1969 | Hardy ......................... 424/359 |
| 3,478,146 | 11/1969 | Balana . |
| 3,551,560 | 12/1970 | Thiele . |
| 3,563,925 | 2/1971 | Kleinert et al. |
| 3,608,071 | 9/1971 | Relyueld et al. ............ 424/88 |
| 3,628,974 | 12/1971 | Battista ....................... 424/359 |
| 3,639,577 | 2/1972 | Urton et al. ................. 424/88 |
| 3,691,281 | 9/1972 | Battista ....................... 424/359 |
| 3,703,575 | 11/1972 | Thiele . |
| 3,767,437 | 10/1973 | Cruz . |
| 3,772,432 | 11/1973 | Balana . |
| 3,773,919 | 11/1973 | Boswell et al. ............. 424/19 |
| 3,787,900 | 1/1974 | McGee ......................... 3/1 |
| 3,790,507 | 2/1974 | Hodash . |
| 3,808,606 | 5/1974 | Tronzo . |
| 3,821,371 | 6/1974 | Battista ....................... 424/359 |
| 3,823,212 | 7/1974 | Chvapil ....................... 264/49 |
| 3,846,542 | 11/1974 | Gross . |
| 3,855,638 | 12/1974 | Pilliar . |
| 3,867,190 | 2/1975 | Schmitt et al. |
| 3,887,699 | 6/1975 | Yolles ......................... 424/19 |
| 3,918,100 | 11/1975 | Shaw et al. . |
| 3,925,545 | 12/1975 | Relyueld ..................... 424/88 |
| 3,949,073 | 4/1976 | Daniels et al. .............. 424/359 |
| 3,976,071 | 8/1976 | Sadek .......................... 128/260 |
| 3,991,766 | 11/1976 | Schmitt et al. ............. 424/335.5 |
| 4,016,252 | 4/1977 | Relyueld ..................... 424/88 |
| 4,032,993 | 7/1977 | Coquard et al. |
| 4,051,598 | 10/1977 | Sneer . |
| 4,131,650 | 12/1978 | Braumer et al. ............ 424/359 |
| 4,141,864 | 2/1979 | Rijke et al. |
| 4,156,943 | 6/1979 | Collier . |
| 4,164,559 | 8/1979 | Miyata et al. .............. 424/14 |
| 4,177,524 | 12/1979 | Grell et al. . |
| 4,191,740 | 3/1980 | Heusser et al. |
| 4,191,743 | 3/1980 | Klemm et al. |
| 4,192,021 | 3/1980 | Deiby et al. |
| 4,195,366 | 4/1980 | Jarcho et al. |
| 4,202,055 | 5/1980 | Reiner et al. |
| 4,239,113 | 12/1980 | Gross et al. |
| 4,291,013 | 9/1981 | Wahlig et al. .............. 424/16 |

FOREIGN PATENT DOCUMENTS

| | | |
|---|---|---|
| 139949 | 1/1971 | Czechoslovakia . |
| 141238 | 5/1971 | Czechoslovakia . |
| 144375 | 6/1972 | Czechoslovakia . |
| 2620890 | 11/1977 | Fed. Rep. of Germany . |
| 2620891 | 11/1977 | Fed. Rep. of Germany . |
| 2620907 | 11/1977 | Fed. Rep. of Germany . |
| 1441817 | 5/1966 | France . |
| 1213054 | 11/1970 | United Kingdom . |
| 1298223 | 11/1972 | United Kingdom . |
| 1541793 | 3/1979 | United Kingdom . |

OTHER PUBLICATIONS

Chvapil et al., International Review of Connective Tissue Research 6:1-61 (1973) "Medical and Surgical Applications of Collagen".
Stenzol et al., Ann. Rev. Biophysics Bioengineering 3:231251 (1974) "Collagen as a Biomaterial".
Nelson et al., Chem. Abstr. 88 #158418Q (1978) of Oral Surg. Oral Med. Oral Pathol. 1977 43(6) 836–843 Evaluation and Comparisons of Biodegradable Substances as Osteoginic Agents.
Lauten Schlager et al., C.A. 86 #34247b (1977).
C.A. 86 #47297t 1977 Gross et al.
Scherico C.A. 81 #29549u (1974).
Koster et al., Langen Becks Arch, Chir. 341:77–86(1976) "Experimental Bone Replacement with Resorbable Calcium Phosphate Ceramic".
Rejda et al., Chem. Abstr. 88 #459y(1978) of J. Bioeng. (1977) 1/2193-7 "Tricalcium Phosphate as a Bone Substitute".
Rubin et al. J. Clin. Pharmacology 13(3):309312, Aug.-/Sep. 1973, "Collagen as a Vehicle for Drug Delivery".
Herde et al., 47 Jahngang Hebt 8(1975), pp. 327–328.
Chem. Abstr. 88:158414q 1978.
Chem. Abstr. 82:103113m 1975.
Chem. Abstr. 92:135160x 1979.
Chem. Abstr. 91:181401d 1979.
Chem. Abstr. 91:208991k 1979.
Chem. Abstr. 88:459y 1978.
Chem. Abstr. 88:177250z 1978.
Chem. Abstr. 89:152615e 1978.
Chem. Abstr. 89:12193r 1978.
Chem. Abstr. 92:203609c 1980.
Chem. Abstr. 88:177250z 1978.
Chem. Abstr. 89:144878c 1978.
Chem. Abstr. 82:47710q 1975.

Chem. Abstr. 83:65343x 1975.
Chem. Abstr. 83:152304d 1975.
Chem. Abstr. 86:34241v 1977.
Chem. Abstr. 87:28970m 1977.
Chem. Abstr. 91:198960h 1979.
Chem. Abstr. 93:210315c 1980.
Chem. Abstr. 92:116473k 1980.
Chem. Abstr. 87:177981t 1977.
Chem. Abstr. 92:82460m 1980.

*Primary Examiner*—Shep K. Rose

*Attorney, Agent, or Firm*—Millen & White

[57] ABSTRACT

A shaped mass resorbable in the body, comprises collagen and a bioresorbable binding agent for collagen, the binding agent being selected, e.g., from polymers of $C_{2-16}$ α-hydroxyalkanoic acids, polymers of natural amino acids, hydrolyzed collagen or hydrolyzed elastin.

6 Claims, No Drawings

MEDICINALLY USEFUL, SHAPED MASS OF COLLAGEN RESORBABLE IN THE BODY

This is a division of application Ser. No. 082,520 filed Oct. 9, 1979, now U.S. Pat. No. 4,291,013.

BACKGROUND OF THE INVENTION

The present invention concerns a shaped mass based on collagen resorbable in the body, its preparation and its use in medicine, especially as surgical material and/or as an active material depot.

It is known to introduce into the body bioresorbable materials, such as collagen, in freeze-dried or foamed form and thus to fill up, e.g., bone or tissue defects. Such implants can be used to stop bleeding and can also be employed for the induction of granulation tissue; however, they have the disadvantage that they are relatively loosely constructed and, therefore, upon moisture take-up, lose their shape relatively quickly. Thus, the body tissues scarcely have time to grow again to a sufficient extent. Therefore, it is desirable to develop similar materials which display the advantages of the known collagen preparations, but simultaneously have a more stable consistency and, therefore, lose their shape less quickly.

It is also known that active materials, such as antibiotics, can be embedded in certain synthetic resins, such as, e.g., polymethacrylates and/or polyacrylates, and are slowly liberated from these non-resorbable carriers when they are used as implantations in the body. Such active material-containing synthetic resins are commercially available, e.g., as spheroids which are implanted near the bone or soft tissue infections to be treated and can provide a sufficiently high active material concentration in situ. This new therapy has proved to be useful in the case of various infections in the body, but has the disadvantage that, in certain cases, the spheroids cannot be left in the organism; on the contrary, after some time, they must be removed, which means a renewed surgical intervention and thus a renewed risk of infection. Therefore, it is also desirable to have an alternate therapeutic principle so that the mentioned removal of the spheroids can be obviated.

From Federal Republic of Germany Patent Specification No. 12 93 396 is also known the use of polyhydroxyacetic acid esters for the production of antibiotic-containing, resorbable surgical stitching materials, tubes and films. Furthermore, in published Federal Republic of Germany patent application No. 20 51 850, there are described pharmaceutical compositions which are characterized in that they contain an active material in combination with a polylactide or a copolymer of lactide and glycolide units.

SUMMARY OF THE INVENTION

Accordingly, it is an object of this invention to provide a collagen composition which can be formed into a shapable mass which is resorbable.

It is a further object of this invention to provide an agent compatible with the body comprising shapable collagen which is suitable as surgical material or as an implantable active material depot with protracted liberation of active material.

It is another object of this invention to provide a production process for such an agent which is acceptably economical and uses easily and cheaply available starting materials.

Upon further study of the specification and appended claims, further objects and advantages of this invention will become apparent to those skilled in the art.

These objects have been attained by providing a shaped mass based on collagen resorbable in the body which comprises collagen and a bioresorbable binding agent for collagen. Furthermore, the resorbable mass can additionally contain an active material, especially an antibiotic and/or calcium phosphate.

This invention also provides a process for the shaping of collagen, which comprises working-up together collagen and a bioresorbable binding agent for collagen, under the action of pressure and/or heat, wherein an active material and/or calcium phosphate can additionally be incorporated. The shaped mass based on collagen of this invention can be worked up at surprisingly low temperatures.

Further aspects of this invention are the use of the resorbable, optionally calcium phosphate-containing mass, as surgical material, or of a mass of this invention additionally containing an active material as an active material depot.

Preferred compositions of this invention are those shaped masses comprising collagen which, as bioresorbable binding agent, contain a copolymer of lactic acid and glycolic acid, especially one in which are contained 10–30 mole % of glycolic acid units. Also preferred are those compositions which, as binding agent, contain a protein produced by hydrolysis of collagen, having an average molecular weight of about 2500–4000. Additionally preferred are also those compositions which function as an active material depot and which contain gentamycin as the active material.

DETAILED DISCUSSION

Collagen, which is not shape-stable under the influence of moisture, is, due to the bioresorbable binding agent of this invention, brought into a shaped mass, i.e., into a permanent shape, without being chemically attacked or changed by this procedure. "Shaping" herein means that the mixture of collagen and binding agent serving as starting material can be worked up into a desired shape under the action of pressure and/or heat manually or by the techniques conventionally employed in the working up of synthetic resins, such as by an injection molding process. For the shaping of the binding agents of this invention, surprisingly comparatively low temperatures are necessary. This temperature can be so adjusted that a comparatively large series of different active materials can be incorporated undecomposed into the mass. This applies especially to the composition of this invention in which the binding agent is a polymer or copolymer of lactide and/or glycolide units or especially of protein which has been prepared by the decomposition of collagen. A gentle working up of the active material is thereby rendered possible.

Contrary to expectations, due to the shaping of the composition according to this invention, there is obtained a fairly hard and mechanically stable material, even when the binding agent content of the mass is relatively small, and, e.g., only amounts to 3–10 wt%.

Depending upon the intended purpose of use, the composition according to this invention can be brought into different shapes. Thus, there are suitable comparatively large shaped bodies which can be brought into the desired shape by cutting or hammering operations. Tubes, strands, foils or tablets in various sizes are, e.g., often expedient as shapes. Especially preferred are spheroidal shaped bodies of various dimensions, e.g., spheroids with a diameter of 0.5–10 mm, preferably 2–7 mm. Also preferred are granulates with a diameter of 0.1–5, preferably of 0.5–2 mm.

The composition according to this invention can also suitably be formed into a powder which can be produced, e.g., by conventional comminution of larger shaped bodies, possibly with admixing of conventional additives, such as talc or starch.

If an active material is present in the composition of this invention, after its implantation into the body, it is, surprisingly, very favorably liberated. Whereas liberation from conventional (e.g., lyophilized) collagen takes place relatively quickly, the active material can be liberated protractedly from the composition of this invention, i.e., over a desired period of time, in the necessary concentrations. The active material is thereby continuously and slowly given off without cell-damaging side effects caused by the implant. In vitro experiments with the preferred compositions of this invention which, as binding agent, contain a copolymer of lactide and glycolide units and, as active material, gentamycin sulphate, have, e.g., shown that the antibiotic is liberated in initially very high, then slowly decreasing concentrations. The amount of the antibiotic liberated and the period of time of the liberation can be controlled by variation of the proportions of the components and of the working-up conditions employed in the production of the composition. The process conditions to be employed are well known to the expert and the desired properties of the process end products can be tested by standard methods.

An addition of a certain percentage of calcium phosphate, especially of tricalcium phosphate, permits an especially uniform liberation of the active material, and is also often otherwise advantageous since calcium phosphate additionally stimulates the growth of bone.

Especially suitable as binding agents of this invention for the collagen are polymers of glycolic acid and lactic acid, as well as their copolymers in various weight ratios of the monomer units. Especially suitable are lactide/glycolide copolymers and a glycolide content of 5–40 mole %, preferably of about 10–30 mole %. Suitable are, furthermore, e.g., also copolymers of α-hydroxybutyric acid and glycolic acid of a glycolic acid content of 25–70 mole % and corresponding copolymers of α-hydroxybutyric acid and lactic acid of a lactic acid content of 40–85 mole %. Copolymers having a content of 40–70 mole % of glycolic acid, 1–15 mole % of α-hydroxybutyric acid and a residual proportion of lactic acid are also suitable.

Quite generally, there are suitable all homo- and copolymers of α-hydroxyfatty acids of 2–16 C-atoms insofar as these are non-toxic and still resorbable in the body, thus, e.g., co- and possibly homopolymers of glycolic acid, lactic acid, α-hydroxybutyric acid, α-hydroxyisobutyric acid, α-hydroxyvaleric acid, α-hydroxyisovaleric acid, α-hydroxycaproic acid, α-hydroxy-α-ethylbutyric acid, α-hydroxyisocaproic acid, α-hydroxy-β-methylvaleric acid, α-hydroxyheptanoic acid, α-hydroxyoctanoic acid, α-hydroxydecanoic acid, α-hydroxymyristic acid, α-hydroxystearic acid and α-hydroxylignoceric acid. The α-hydroxy fatty acids can be present wholly or partially in optically-active forms (e.g., D- or L-forms) or in optically-inactive (DL- or racemic) form, thus lactic acid as D-, L- or DL-lactic acid. The amount ratio between the monomer units in the copolymers is in principle unlimited, but copolymers containing higher weight α-hydroxycarboxylic acids are, as a rule, more difficult to resorb than polymers containing lower α-hydroxyfatty acids. Thus, copolymers consisting of α-hydroxyvaleric acid and glycolic acid, e.g., are composed mainly of units of glycolic acid, e.g., of 90 wt % glycolic acid and 10% α-hydroxyvaleric acid. This also applies similarly to copolymers with the other mentioned α-hydroxyfatty acids.

Other resorbable binding agents include those which are derived from polyamino acids having a molecular weight of about 2000–8000, whereby the molecular weight can, however, exceed these limits upwardly or downwardly. Among these are preferred hydrolytically produced decomposition products of collagen or also of elastin and similar proteins, which products possess a molecular weight of about 2500–4000, preferably of about 3000. Conditions employed for such hydrolyses are conventional and are disclosed, for example, in Treatise on Collagen, G. N. Ramachandran, Gen. Ed. (Academic Press, New York, 1967) whose disclosure is incorporated by reference herein.

Also usable are resorbable, synthetically produced polyamino acids of about the same molecular weight, e.g., of proline, hydroxyproline and/or glycine units. However, it is also possible to employ other polymers and copolymers of, e.g., natural amino acids, e.g., of alanine, lysine, glycine, valine, leucine, isoleucine, phenylalanine, serine, threonine, cysteine, methionine, asparagine, glutamine, arginine, histidine, proline, hydroxyproline and/or other amino acid units.

Equivalent suitable agents for the collagen include, in principle, all polymers which are bioresorbable, i.e., which are broken down or resorbed in the body.

In the resorbable mass of this invention, the ratio between collagen and the binding agent can be varied within wide ranges. However, those compositions are preferred in which the proportion of the binding agent is 1–25, preferably 3–10, and especially about 5 wt % of the total amount of collagen and binding agent. Especially preferred are those compositions in which the least possible amount of binding agent is contained but which, nevertheless, are still shapable, i.e., those which contain the minimum amount effective for rendering the composition shapable.

Those compositions are also preferred which can be shaped at the lowest possible temperature, e.g., at temperatures of from room temperature to 200° C., preferably of 70°–110° C.

Especially preferred are compositions of about 90–96 wt % of collagen and about 10–4 wt % of hydrolyzed collagen (protein powder with a molecular weight of about 3000) which, under certain conditions, can already be shaped at temperatures of 80°–100° C.

Quite generally, among the compositions of this invention, those are also preferred in which the binding agent possesses a reduced specific viscosity (i.e., the ratio between specific viscosity and concentration) of 10–450, preferably of over 30 cm$^3$/g.

The expression "active material" is used herein in a very wide sense and includes all articles which are intended, by parenteral routes, for the healing, amelioration, treatment and/or prevention of health disturbances in patients, e.g., humans, and animals, e.g., mammals, ore are able to influence a function of the body of humans or animals.

In particular, there are to be mentioned antibacterially active materials of various kinds, especially antibiotics. These are to be stable, especially chemically stable, towards the resorbable mass of the invention and especially its individual components and otherwise system compatible. Their activity spectrum includes gram-positive or gram-negative pathogens or preferably both groups. The active materials are, as far as possible, to bring about no or only a delayed resistance in the pathogens. Among the antibacterially active materials, the following antibiotics are mentioned by way of example: aminoglycoside antibiotics, such as amikacine, butirosin, didesoxykanamycin B (DKB), fortimycin, gentamycin, kanamycin, lividomycin, neomycin, Netilmycin, ribostamycin, sagamycines, seldomycins and their epimers, sisomycin, sorbistin, tobramycin; chloroamphenicol and derivatives, such as thiamphenicol; erythromycins; lactone antibiotics, such as novobiocin; leucomycins, such as josamycin, maridomycin, midecamycin, spiramycin; lincomycins, such as clindamycin, lincomycin; macrolides, such as rosamycin; penicillins, such as amoxicillin, ampicillin, azlocillin sodium, dicloxacillin sodium, furoxacillin, mecillinam, piperacillin; peptide antibiotics, such as bacitracin, colistimethate sodium, gramicidin, polymyxins; rifamycins, such as rifampicin, rifamycin; steroid antibiotics, such as fusidic acid; trimethoprim; streptomycins; tetracyclones, such as doxycyclin, minocyclin, tetracyclin; cephalosporins, such as cefalothin, cefamandol, cefazedone, cefazolin, cefoxitin, cefuroxime; as well as other antibiotics, e.g., cycloserine, fosfomycin, vancomycin, etc. The aminoglycoside antibiotics, especially gentamycin, are thereby especially suitable because of their wide antibacterial spectrum and their heat stability.

It is also possible to combine two or more of these antibiotics with one another, e.g., gentamycin with clindamycin; combinations of these antibiotics with other active materials, e.g., with antiseptics, are also suitable.

Further suitable antibacterially active materials are, e.g., sulphonamides (such as sulphadiazine), as well as tuberculosis and leprosy agents (such as aminosalicyclic acid of sulphones).

Also preferred are active materials for other indications, e.g., antiseptics (such as bromochlorophen, hexetidine, buclosamide, salicyclic acid, cerium nitrate, chlorhexidine, 5-chloro-8-hydroxyquinoline, copper 8-hydroxyquinolate, acridine orange, undecenoic acid, undecoylium chloride, silver salts, such as silver sulphadiazine, mafenide, nitrofurazone, cloflucarban, tribromsalan, tauroline, noxythioline, etc., furthermore inflammation inhibitors (such as salicylates, phenylbutazone, indomethacin, ibuprofen, p-aminophenol derivatives [e.g., acetaminophen], pyrazolones, hydrocortisone palmitate, etc.), as well as cytostatics (such as fluorouracil, vinblastin, doxorubicin, prednisone, etc.).

The amount of the active material to be added can be varied over wide ranges and depends essentially upon its activity. In generaly, the amount of the active material is about 0.2-20 wt %, preferably at about 2-10 wt %, referred to the bioresorbable mass.

For gentamycin, e.g., additions of 1-4 wt. % have proved to be especially favorable (calculated on the basis of gentamycin base). The other active materials are preferably admixed in amounts which are adequate for their activity. Active material mixtures can thereby also be chosen.

According to the invention, the resorbable compositions can also contain calcium phosphate, especially tricalcium phosphate. This additive can be present in an amount of 0.1-40 wt% based on the weight of resorbable mass. Preferred are calcium phosphate contents of about 1-25, and especially of 5-about 20 wt %. Especially suitable is, e.g., a precipitated crystalline calcium phosphate material, the particles of which can be up to about 1 mm in dimension. Preferred are particle diameters of between 0.02 and 0.25 mm. Amorphous, molten, vitreous and/or sintered calcium phosphate of about the same particle size is also usable. The calcium phosphate, especially tricalcium phosphate, is employed as a bioactivating additive. As is known, it stimulates the growth of bone and has, astonishingly, a favorable action on the protracted liberation of the active material. Calcium phosphate additions are, in particular, expedient in the case of those compositions of the invention which are to serve as surgical material in the healing and supplementing of bone.

For the production of the composition of this invention, collagen and the bioresorbable binding agent for collagen can be worked up with one another in various ways. In the simplest case, these materials are directly mixed with one another and then worked up. If calcium phosphate is to be present, then, here, too, it can be worked by this same simple process which, for economic reasons, is itself preferred. However, for the better embedding of the calcium phosphate, it can first be worked up with the binding agent and then this premixture can be pressed and/or sintered together with the collagen.

For the production of an active material-containing composition of this invention, numerous possibilities are also available. The working up of a previously prepared mixture of all components is itself preferred. For effecting this process, e.g., collagen, the binding agent, the active material, and optionally calcium phosphate, are carefully mixed with one another and homogenized. The powder obtained is then melted and/or sintered under pressure and/or heat.

The temperatures—depending upon the heat stability of the active material and/or of the binding agent—can thereby be varied over a wide range, e.g., from room temperature to 200° C. If the binding agent consists, e.g., of copolymers of glycolic acid and lactic acid units, temperatures of about 130° to 170° C. are preferred. If, on the other hand, a proteinaceous material, e.g., of hydrolyzed collagen, is employed as binding agent, then lower temperatures, e.g., 40°-90° C., preferably 60°-85° C., are advantageous but, of course, higher temperatures can be employed if necessary for technical reasons.

The work-up of the components can also be carried out in such a manner that the active material—with or without calcium phosphate—is first melted, sintered or pressed with the binding agent (e.g., the copolymers of glycolic acid and lactic acid units), whereupon the resulting, relatively active material-rich premixture is cooled and comminuted, e.g., by grinding. Thereafter occurs the admixing with collagen and, optionally, additional active material, and the final work-up under the influence of pressure and/or heat. Compositions of this invention which are prepared according to this process frequently display a better and more uniform liberation of active material and are, therefore, sometimes preferred in comparison with those produced according to the simple mixing process.

For the preparation of the premixtures, possibly lower temperatures can be used than for the final shaping under the above-stated conditions.

When calcium phosphate is used, it can be worked up, together with the active material, with the premixture or can be first admixed at the final shaping. The first-mentioned process has the advantage that the mixing of the active material with calcium phosphate is especially intimate, from which results a favorably protracted liberation of the active material in implantations, e.g., in bones.

The final shaping of the process components of this invention can be carried out according to all conventional processes of synthetic resin technology which permit the production of solid shaped parts under the action of pressure and/or heat. Very favorable is, e.g., the pressure technique in which pressures of 300–1200, preferably of about 600–750 bar are employed. In this method, the compositions are brought into the desired shape using negative molds of, e.g., metal. Work-up is also possible according to the technically very advantageous injection molding process, with which numerous different shapes can be formed. Very suitable is also the extrusion process which, in contradistinction to the previously mentioned processes, operates continuously. Thereby can be obtained, e.g., strands, fibers, tubes, pipes and foils which can subsequently be divided up or comminuted in any desired manner. Another suitable process for shaping is the impact sinter process according to which the material to be shaped is briefly heated up and is sintered together by sudden application of pressure. The sintering frequently only takes place on the surface of the substance grains. In this manner, the working up temperatures are comparatively low and permit a substantial protection of the active material to be embedded. Other work-up techniques are also applicable, e.g., the "cold sintering together" by ultrasonics.

The compositions of this invention can be employed as active material depot or as surgical materials, e.g., as bond material (alone or in conjunction with spongiosa) for bone breakages or shatterings. A content of calcium phosphate and especially of tricalcium phosphate can stimulate the bone growth and is, therefore, expedient even though not absolutely essential. A certain content of antibiotic is also favorable for the prevention of infections, e.g., of 1–5 wt.%. As shaped parts, small plates, spheres of various size and granulates are preferred.

The active material-containing compositions of this invention are also preferred as active material depot. If the active material is an antibiotic, then the composition is suitable, e.g., for the prophylaxis of infection in the case of contaminated, comparatively extensive soft tissue wounds or in the case of smashed zones of open bone breakages, such as frequently occur in the case of accidents. Infected wound cavities can be well closed off and filled up with these agents. It is thereby possible to apply active materials and especially antibiotics locally in depot form, i.e., directly at the infected or endangered places.

Advantageously, in the case of this embodiment, the composition of this invention generally needs only to be applied a single time since it is fully resorbed in the course of time. Therefore, it is no longer necessary to remove the implant after the healing of the wound.

A further field of use for the antibiotic-containing compositions of this invention is in bone surgery, especially the treatment of post-traumatic osteomyelitis. The new agent is very well suited—especially when containing calcium phosphate and particularly tricalcium phosphate—for the filling up of osteomyelitic holes. Simultaneously with the gradual resorption of the implant of this invention, the newly forming tissue will be grown into it, whereby there results a healing process as in an aseptic medium.

The antibiotic-containing new agent is also suitable as an aseptic carrier for the transplantation of a patient's own spongiosa. For this purpose, e.g., an antibiotic-containing granulate of this invention is introduced with the patient's own spongiosa into the infected bone cavity. In comparison with the conventional methods, this has the advantage that, because of the local presence of the antibiotic, an infection will result less easily or to a lesser extent. Therefore, unlike the conventional mode, the implantation need not be repeated one or more times. The loss of the spongiosa, which is only available to a limited extent, is thereby reduced.

In the case of an implantation, the wound cavity in the bone or in the tissue is carefully filled up with the composition of this invention and, in this way, closed off. A comparatively large piece of the composition of this invention can thereby be exactly adapted to the wound or, the cavity can be filled with smaller dimensioned particles or spheres. By suitable dimensionsing of the particles, an optimum filling can thereby be achieved. After application of the antibiotic-containing agent of this invention, the purulent secretion in the treatment of osteomyelitis is overcome comparatively quickly. With the composition of this invention, filled wound cavities no longer display any indications of inflammation after some time. Insofar as calcium phosphate is present, the resorption can thereby be easily controlled and monitored since the calcium phosphate particles can be easily recognized in an X-ray.

Apart from the antibiotic-containing compositions of this invention, those compositions are preferred in which antiseptics or inflammation inhibitors are present. In all of these cases, for the use at specific locations of the body, relatively high active material concentrations can be achieved. This local action is, in many cases, desired and represents an especial advantage of this invention. Finally, the use of the active material-containing compositions of this invention takes place in about the same way as the use of the previously known products employed for the same purpose.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1 (Tablets)

A mixture of 475 g of finely ground collagen, 25 g of a copolymer of 80 mole % L-lactide and 20 mole % glycolide, with a reduced specific viscosity of 42 cm$^3$/g and 10 g of gentamycin sulphate is well homogenized. The mixture is subsequently pressed in a heated press at 135° C. under a pressure of about 630 bar for one minute in a metal negative mold to produce tablets with a diameter of 1 cm and a height of 2 mm; each tablet contains 93 wt % of collagen, 5 wt % of copolymer and about 2 wt % of gentamycin sulphate.

A sterilization, e.g., by gassing with ethylene oxide or irradiation, can optionally follow. The tablets can be employed for the prophylaxis of infection in the case of soft tissue wounds or zones of destruction in the case of open bone breakages or also for the filling of osteomyelitic cavities.

EXAMPLE 2 (Tablets)

Analogously to Example 1, 425 g of collagen and 25 g of a copolymer of 80 mole % L-lactide and 20 mole % glycolide, with a reduced specific viscosity of 42 cm$^3$/g are worked up to a platelet (1×3×0.5 cm). The platelet contains 95 wt % of collagen and 5 wt % of copolymer.

EXAMPLE 3 (Granulate)

A mixture of 375 g of finely powdered collagen, 25 g of a copolymer of 70 mole % L-lactide and 30 mole % glycolide, with a reduced specific viscosity of 53 cm$^3$/g, 100 g of finely powdered tricalcium phosphate and 10 g of gentamycin sulphate is well homogenized and subsequently shaped in a heated extruder at a mass temperature of about 145° C. to give a strand of 1.5 mm diameter which is subsequently chopped up into 1 mm lengths to give a granulate. This contains 74 wt % of collagen, 5 wt % of the copolymer, 19 wt % of tricalcium phosphate and about 1.9 wt % of gentamycin sulphate. The cylinder-shaped particles have a diameter of about 1 mm and a length of about 1.5 mm.

Sterilization is optional, analogously to Example 1.

EXAMPLE 4 (Platelets)

25 g of a copolymer of 80 mole % L-lactide and 20 mole % glycolide, with a reduced specific viscosity of 60 cm$^3$/g is heated together with 10 g of gentamycin sulphate to 135°–145° C. until an outwardly homogeneously appearing metal results. After cooling, the solidified melt is finely powdered and mixed with 475 g of collagen. This mixture is shaped into platelets with a size of 1×2.5×0.4 cm at a mass temperature of about 165° C. with an injection molding machine. The platelets contain 93 wt % of collagen, 5 wt % of the copolymer and about 1.9 wt % of gentamycin sulphate.

Sterilization can be performed analogously to Example 1.

EXAMPLE 5 (Spheroids)

A mixture of 475 g of collagen, 25 g of a hydrolyzed water-soluble collagen (protein powder) with an average molecular weight of about 3000 and 10 g of gentamycin sulphate is pressed analogously to Example 1, but at 86° C. to give spheroids with a diameter of about 7 mm. The spheroids contain 93 wt % of collagen, 5 wt % of hydrolyzed collagen (protein powder) and 2 wt % of gentamycin sulphate.

Sterilization can be performed analogously to Example 1.

EXAMPLE 6 (Spheroids)

A mixture of 25 g of a hydrolyzed water-soluble collagen (protein powder) with an average molecular weight of about 3000, 10 g of gentamycin sulphate and 100 g of finely powdered tricalcium phosphate is pressed at about 650 bar and 90° C. for two minutes. The pressed material is subsequently ground and the resultant powder mixed up with 375 g of finely powdered collagen. The mixture is subsequently pressed for 1 minute at about 650 bar and 85° C. to give spheroids with a diameter of about 6 mm. The spheroids contain 74 wt % of collagen, 5 wt % of protein powder, about 19 wt % of tricalcium phosphate and about 1.9 wt % of gentamycin sulphate.

Sterilization can be performed analogously to Example 1.

EXAMPLE 7 (Spheroids)

A mixture of 475 g of finely ground collagen, 25 g of a copolymer of 90 mole % L-lactide and 10 mole % of glycolide with a reduced specific viscosity of 48 cm$^3$/g, and 15 g of gentamycin sulphate is well homogenized. The powder obtained is sintered at 150° C. under a pressure of about 600 bar for 2 minutes into the desired shape, preferably spheroids of 7–10 mm diameter or rodlets of 1.5 cm length and 0.5 mm diameter. The shaped particles contain 92 wt % of collagen, about 5% of copolymer and 2.9% of gentamycin sulphate.

EXAMPLE 8 (Granulate)

A mixture of 450 g of collagen, 50 g of a water-soluble protein powder with an average molecular weight of about 4000 (prepared by hydrolysis of collagen) and 80 mg of 9α-fluoro-16-methyleneprednisolone 21-acetate is shaped in a heated extruder at a mass temperature of about 80° C. to a strand of 1 mm diameter which is subsequently chopped up in lengths of 0.9 mm to give a granulate. This contains 89 wt % of collagen, about 9.4 wt % of protein as binding agent and about 1.6 wt % of 9α-fluoro-16-methyleneprednisolone 21-acetate and can optionally be sterilized analogously to Example 1. The particle size is about 1×1×0.9 mm.

EXAMPLE 9 (Powder)

A mixture of 450 g of collagen, 50 g of a water-soluble protein powder (molecular weight about 3000, prepared by hydrolysis of collagen or elastin) and 120 mg of 9α-fluoro-16-methyleneprednisolone 21-acetate is shaped in a heated extruder at a mass temperature of about 80° C. to give a strip of 1 cm breadth and 1 mm height and subsequently comminuted by cutting and grinding. The product is ground, together with 50 g of maize starch and 50 g of talc, to a fine powder which, in total, contains 72 wt % of collagen, 8.2 wt % of protein binder, 2 wt % of 9α-fluoro-16-methyleneprednisolone 21-acetate, 8.2 wt % of maize starch and 9.2 wt % of talc.

Sterilization can be performed analogously to Example 1.

EXAMPLE 10 (Spheroids)

A mixture of 450 g of collagen, 25 g of copolymer of glycine and alanine with a molecular weight of about 3000 (50 mole % each of the monomers) and 100 mg of gentamycin sulphate is homogenized and pressed in a heated press at 195° C. under a pressure of about 700 bar for 1 minute in a negative mold of metal to give spheroids with a diameter of 3 mm. Each spheroid contains 93 wt % of collagen, 5 wt % of polyalanineglycine and about 2 wt % gentamycin sulphate.

Sterilization can be performed analogously to Example 1.

EXAMPLE 11 (Tablets, Impact Sintered)

A mixture of 475 g of finely ground collagen, 25 g of a copolymer of 70 mole % L-lactide and 30 mole % glycolide, with a reduced specific viscosity of 80 cm$^3$/g and 10 g of gentamycin sulphate is well homogenized. The mixture is subsequently briefly heated up in an impact sintereing device to 150° C. and sintered together by sudden pressing together. In the case of this procedure, the average temperature in the particles lies at about 50°-60° C. It is cooled for about 10 seconds and possibly sterilized analogously to Example 1. Each tablet has a diameter of 6 mm and a height of 2.5 mm; it contains 93 wt % of collagen, 5 wt % of copolymer and about 2 wt % of gentamycin sulphate.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A collagen based drug delivery system which is resorbable in the body, is sterilized and has been compacted into the shape of a tablet, spheroid, foil, pipe, plate, fiber, granule, strand or tube implantable into the body, by the application of heat of a temperature of 40°-200° C., optionally also with application of pressure of 300-1200 bar, with extrusion, with injection molding or with sintering and which, upon administration to the body, essentially maintains its shape and effects a retarded liberation of the drug, comprising 0.2-20 weight percent of a pharmacologically active drug material, 1-25 weight percent of a bioresorbable binding agent for collagen, and the balance being finely ground collagen, the binding agent consisting essentially of a co- or homopolymer of natural amino acids or of hydrolyzed collagen or hydrolyzed elastin.

2. The resorbable drug delivery system of claim 1, further comprising 0.1-40% by weight of the resorbable mass of calcium phosphate.

3. The resorbable drug delivery system of claim 1, wherein the binding agent is a hydrolyzed collagen or hydrolyzed elastin of a molecular weight of about 2500-4000.

4. The resorbable drug delivery system of claim 1, comprising
   3-10 wt. % of the binding agent based on the total amount of collagen and binding agent; and
   1-10% by weight of the resorbable mass of the pharmacologically active material.

5. A method of administering a pharmacologically active material to a patient in need of treatment with the active material which comprises administering an effective amount of the active material in the form of a drug delivery system of claim 1.

6. The method of claim 5, wherein the administration is during a surgical procedure.

* * * * *